United States Patent [19]

Fleming et al.

[11] 4,064,347
[45] Dec. 20, 1977

[54] BIS-BASIC KETONES OF FLUORENE AND FLUORENONE

[75] Inventors: Robert W. Fleming, Wyoming; Arthur D. Sill, Greenhills; William L. Albrecht; Stephen W. Horgan, both of Cincinnati, all of Ohio

[73] Assignee: Richardson-Merrell Inc., Wilton, Conn.

[21] Appl. No.: 328,912

[22] Filed: Feb. 2, 1973

Related U.S. Application Data

[63] Continuation of Ser. No. 23,468, March 27, 1970, abandoned.

[51] Int. Cl.² .................................................. C07D 295/10
[52] U.S. Cl. ........................... 544/79; 260/239 B; 260/268 TR; 260/293.62; 260/326.5 C; 260/570.5 P; 424/248.57
[58] Field of Search ........ 260/246 B, 293.62, 570.5 P, 260/268 TR, 326.5 C, 239 B

[56] References Cited

U.S. PATENT DOCUMENTS

| | | | |
|---|---|---|---|
| 2,783,216 | 2/1957 | Martin | 260/570.5 |
| 2,840,558 | 6/1958 | Martin | 260/247.5 |
| 3,083,201 | 3/1963 | Anderson | 260/346.2 |
| 3,231,629 | 1/1966 | McCall et al. | 260/329.3 |
| 3,251,733 | 5/1966 | Bindler et al. | 260/329.3 |

FOREIGN PATENT DOCUMENTS 286,688 5/1929 United Kingdom.

Primary Examiner—Donald G. Daus
Assistant Examiner—Jose Tovar
Attorney, Agent, or Firm—George W. Rauchfuss, Jr.; Eugene O. Retter

[57] ABSTRACT

The novel bis-basic ketones of fluorene and fluorenone of the present invention have antiviral activity when administered orally and parenterally. These compounds are represented by the following formula:

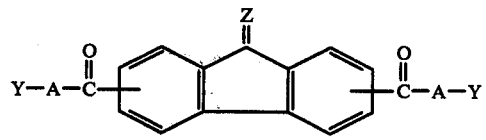

wherein Z is oxygen or $H_2$; each A is a straight or branched alkylene chain having from 1 to about 6 carbon atoms; and each Y is A. the group

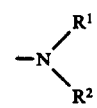

wherein $R^1$ and $R^2$ are individually hydrogen, (lower)alkyl having from 1 to about 6 carbon atoms, cycloalkyl having from 3 to 6 carbon atoms, alkenyl of from 3 to 6 carbon atoms and having the vinyl unsaturation in other than the 1-position of the alkenyl group; or B. the group

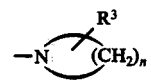

wherein $n$ is a whole integer from 4 to 6, and $R^3$ is hydrogen, (lower)alkyl of 1 to about 4 carbon atoms, phenyl, or benzyl and can be linked to any one of the carbon atoms of the heterocyclic group; or C. the group

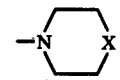

wherein X is oxygen or $NR^4$, and $R^4$ is hydrogen or (lower)alkyl of from 1 to about 4 carbon atoms; or D. the group

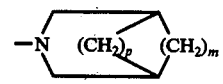

wherein $p$ is a whole integer from 2 to 3, and $m$ is a whole integer from 1 to 2; or a pharmaceutically acceptable acid addition salt of said base.

These new compounds may be prepared by several different methods which are described.

27 Claims, No Drawings

BIS-BASIC KETONES OF FLUORENE AND FLUORENONE

This is a continuation of application Ser. No. 23,468, filed Mar. 27, 1970, now abandoned.

This invention relates to novel bis-basic ketones of fluorene and fluorenone, their method of preparation and use as antiviral agents. Further, many of the compounds of this invention are useful intermediates for the preparation of other pharmaceutically valuable compounds. For example, the fluorenes can be oxidized to the corresponding fluorenones.

The compounds of this invention include both the base form and pharmaceutically acceptable acid addition salts of the base wherein the base form is represented by the general formula

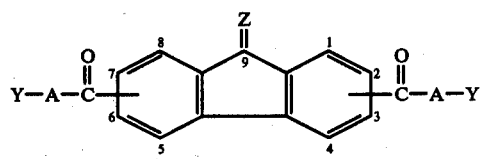

Formula I wherein Z is oxygen or $H_2$; each A is a straight or branched alkylene chain of from 1 to about 6 carbon atoms; and each Y is A. the group

wherein $R^1$ and $R^2$ are individually hydrogen, (lower)alkyl having from 1 to about 6 carbon atoms, cycloalkyl having from 3 to 6 carbon atoms, alkenyl of from 3 to 6 carbon atoms and having the vinyl unsaturation in other than the 1-position of the alkenyl group; or B. the group

wherein $n$ is a whole integer from 4 to 6, and $R^3$ is hydrogen, (lower)alkyl of from 1 to about 4 carbon atoms, phenyl, or benzyl and can be linked to any one of the carbon atoms of the heterocyclic group; or C. the group

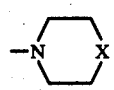

wherein X is oxygen or $NR^4$, and $R^4$ is hydrogen or (lower)alkyl of from 1 to about 4 carbon atoms; or D. the group

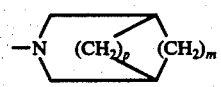

wherein $p$ is a whole integer of 2 or 3, and $m$ is a whole integer of 1 or 2.

The compounds of this invention can be (a) fluorenes when Z represents $H_2$ and (b) fluorenones when Z represents O as is apparent from the following formulas, respectively, wherein A and Y have the meaning given hereinbefore:

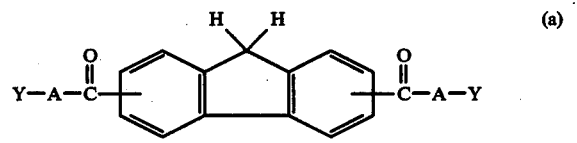

(a)

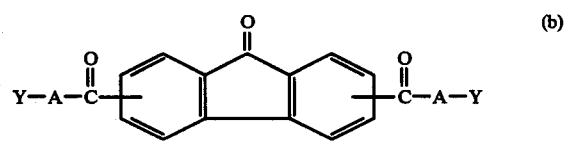

(b)

The basic ketone groups, that is,

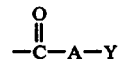

of Formula I can be linked to the tricyclic ring system of fluorene or fluorenone by replacement of any of the four hydrogens of the benzenoid ring to which such group is attached. Thus, one of the groups will be in any of the positions of 1 through 4 of the tricyclic ring system, and the other will be in any of the positions 5 through 8. Preferably one of the basic ketone groups is in the 2-position and the other in the 7-position of the tricyclic ring system.

It is apparent from the above Formula I and its description that compounds can have structures wherein Y is the group

as more fully shown by the following general Formula II, or wherein Y is the group

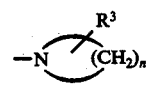

as more fully shown by the following general Formula III, or wherein Y is the group

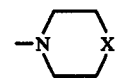

as more fully shown by the following general Formula IV, or wherein Y is the group

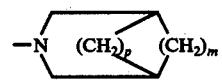

as more fully shown by the following general Formula V below:

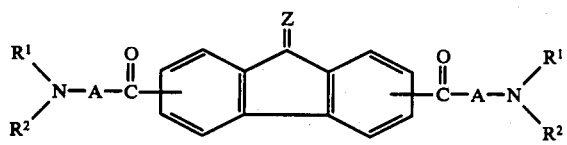

Formula II

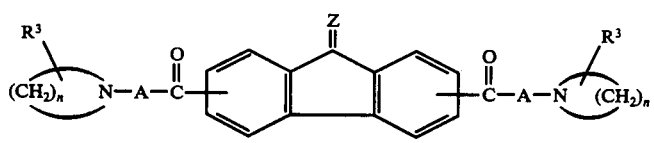

Formula III

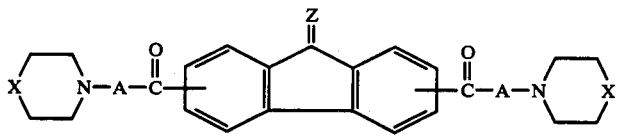

Formula IV

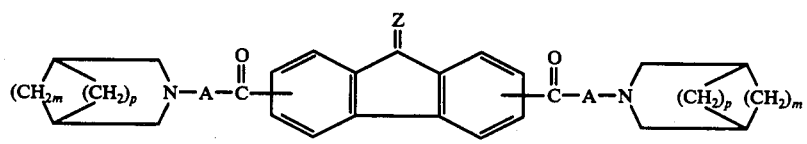

Formula V

In the general Formulas II, III, IV and V the various symbols, Z, A, $R^1$, $R^2$, $R^3$, X, n, m, and p have the meanings given hereinbefore.

Each of the symbols A in the compounds of the above Formulas II, III, IV, and V is an alkylene group having from 1 to about 6 carbon atoms which can be a straight chain, that is, for example, $-CH_2-(CH_2)_s-$ wherein s is a whole integer from 0 to 5, or a branched chain. Each of the alkylene groups as represented by A can be the same or different. Preferably these groups are the same. Illustrative of alkylene groups as represented by A there can be mentioned for example: methylene, 1,2-ethylene, 1,3-propylene, 1,4-butylene, 1,5-pentylene, 1,6-hexylene, 2-methyl-1,4-butylene, 2-ethyl-1,4-butylene, 3-methyl-1,5-pentylene and the like.

Each amino group of the compounds of Formula II, that is,

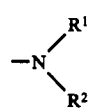

can be a primary, a secondary or a tertiary amino group. Each $R^1$ and $R^2$ is individually hydrogen, (lower)alkyl having from 1 to about 6 carbon atoms, cycloalkyl having from 3 to 6 carbon atoms, alkenyl of from 3 to 6 carbon atoms and having the vinyl unsaturation in other than the 1-position of the alkenyl group. Preferably each of the amino groups as represented by

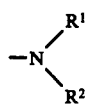

is a tertiary amino group.

The term (lower)alkyl as used in reference to the compounds of Formula II relates to straight or branched alkylene chains having from 1 to about 6 carbon atoms. Illustrative of (lower)alkyls as can be represented by each $R^1$ or $R^2$ in the compounds of Formula II there can be mentioned for example: methyl, ethyl, n-propyl, isopropyl, n-butyl, secondary-butyl, n-amyl, isoamyl, n-hexyl and the like.

Illustrative of cycloalkyl groups as represented by each $R^1$ and $R^2$ in the compounds of Formula II there can be mentioned for example: cyclopropyl, cyclobutyl, cyclopentyl, and cyclohexyl.

When $R^1$ or $R^2$ in the compounds of Formula II represents an alkenyl group, the vinyl unsaturation is in a position other than the 1-position of said alkenyl group. Illustrative of alkenyl groups as can be represented by $R^1$ or $R^2$ there can be mentioned for example: alkyl, 3-butenyl, 4-hexenyl and the like.

Each heterocyclic group of Formula III, that is,

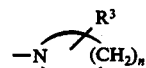

can be a monocyclic heterocyclic group such as those generally equivalent to di(lower)alkylamino groups in the pharmaceutical arts or substituted monocyclic heterocyclic groups. The heterocyclic groups in the compounds of Formula III can be 5-, 6- or 7-membered rings, that is, n is 4, 5 or 6. The $R^3$ group can be hydrogen, a straight or branched (lower)alkyl chain of from 1 to about 4 carbon atoms, phenyl, or benzyl and can be attached to any one of the heterocyclic carbon atoms. Illustrative of heterocyclic groups as represented by each

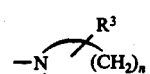

there can be mentioned for example: piperidino, pyrrolidino 4-methylpiperidino, 3-methylpiperidino, 4-tert-butylpiperidino, 4-benzylpiperidino, 4-phenylpiperidino or the like.

Each heterocyclic group of Formula IV, that is,

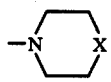

in addition to the one nitrogen atom, contains a second hereto atom, that is, X is O or N-R⁴. The R⁴ group can be hydrogen or a straight or branched (lower)alkyl chain of from 1 to about 4 carbon atoms. As examples of heterocyclic groups as represented by

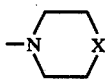

there can be mentioned for example: morpholino, piperazino, N-(lower)alkylpiperazino, such as, for example N-methyl- or N-ethylpiperazino and the like.

Each bicyclic heterocyclic group in the compounds of Formula V, that is,

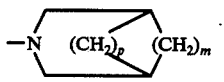

can be an 8-, 9- or 10-membered ring, that is, $p$ is from 2 to 3, and $m$ is from 1 to 2. As examples of such bicyclic heterocyclic groups there can be mentioned for example: 3-azabicyclo[3.2.2]nonan-3-yl, and the like.

Illustrative of base compounds of this invention as represented by Formula I there can be mentioned for example: 2,7-bis(4-aminobutyryl)fluorene, 2,7-bis(4-ethylaminobutyryl)fluorene, 2,7-bis(4-dibutylaminovaler-yl)fluorene, 2,7-bis(4-diethylaminobutyryl)fluorene, 1,7-bis(4-diethylaminobutyryl)fluorene, 2,7-bis(6-piperidinocaproyl)fluorene, 2,7-bis(5-piperidino-4-methylvaleryl)fluorene, 2,7-bis(4-morpholinobutyryl)-fluorene, 2,7-bis(5-piperidino-3-methylvaleryl)fluorene, 2,7-bis[4-(4-methylpiperidino)butyryl]fluorene, 2,7-bis(-piperidinoacetyl)fluorene, 2,7-bis(3-piperidinopropionyl)fluorene, 2,7-bis[5-(3-azabicyclo[3.2.2]non-3-yl)valeryl]fluorene, 2,5-bis-(4-piperidinobutyryl)fluorene, 2,7-bis[4-(4-phenylpiperidino)butyryl]fluorene, 2,7-bis[4-(4-benzylpiperidino)butyryl]fluorene, 2,7-bis(4-diethylaminobutyryl)fluoren-9-one, 2,7-bis(4-piperidinobutyryl)fluoren-9-one, 2,5-bis-[5-(4-benzylpiperidino)valeryl]fluoren-9-one, 2,7-bis(3-morpholinopropionyl)-fluoren-9-one and the like.

Pharmaceutically acceptable acid addition salts of the base compounds of this invention are those of any suitable inorganic or organic acids. Suitable inorganic acids are for example, hydrochloric, hydrobromic, sulfuric or phosphoric acids and the like. Suitable organic acids are, for example, lower aliphatic hydrocarbon monocarboxylic acids, such as, glycolic or lactic acid and the like, lower aliphatic lower alkoxyhydrocarbon monocarboxylic acids, such as, methoxyacetic or ethoxyacetic acids and the like, lower aliphatic lower alkanoyl-hydrocarbon monocarboxylic acids, such as, pyruvic acid and the like, lower aliphatic hydrocarbon dicarboxylic acids, such as malonic, succinic, methylsuccinic, glutaric, α-methylglutaric, β-methylglutaric, itaconic, maleic, citraconic homocitraconic, or fumaric acid and the like, lower aliphatic hydroxy hydrocarbon dicarboxylic acids, such as, malic or tartaric acid and the like, lower aliphatic lower alkoxy-hydrocarbon dicarboxylic acids, such as, α,-β-dimethoxysuccinic or ethoxymaleic acid and the like, lower aliphatic hydrocarbon tricarboxylic acids, such as, aconitic or tricarballylic acid and the like, lower aliphatic hydroxy-hydrocarbon tricarboxylic acids, such as, citric acid and the like. Furthermore, organic sulfonic acids, such as lower alkane sulfonic acids, for example, methanesulfonic or ethanesulfonic acid and the like, or lower hydroxy-alkane sulfonic acids, for example, 2-hydroxyethane sulfonic acid and the like, may be suitable. Particularly useful are pharmacologically acceptable acid addition salts with mineral acids, such as, hydrochloric acid and the like. Mono- or di-acid salts may be formed; also, the salts can be hydrated, for example, monohydrate, or substantially anhydrous.

The compounds of the present invention can be administered to animals such as warm-blooded animals and particularly mammals to prevent or inhibit infections of: picronaviruses, for example, encephalomyocarditis; myxo-viruses, for example, Influenza A₂ (Jap/305); arboviruses, for example, Semliki Forest; herpesvirus group, for example, herpes simplex; and poxviruses, for example, Vaccinia IHD. When administered prior to infection, that is, prophylactically, it is preferred that the administration be within 0 to 96 hours prior to infection of the animal with pathogenic virus. When administered therapeutically to inhibit an infection, it is preferred that the administration be within about a day or two after infection with pathogenic virus.

The dosage administered will be dependent upon the virus for which treatment or prophylaxis is desired, the type of animal involved, its age, health, weight, extent of infection, kind of concurrent treatment, if any, frequency of treatment and the nature of the effect desired. Illustratively, dosage levels of the administered active ingredients can be: intravenous, 0.1 to about 10 mg/kg; intraperitoneal, 0.1 to about 50 mg/kg; subcutaneous, 0.1 to about 250 mg/kg; orally, 0.1 to about 500 mg/kg and preferably about 1 to 250 mg/kg; intranasal instillation, 0.1 to about 10 mg/kg; and aerosol, 0.1 to about 10 mg/kg of animal body weight.

The compounds may be administered, dissolved or suspended, in any conventional non-toxic pharmaceutical carrier of the type that may be taken orally, applied topically, buccally or parenterally.

One of the methods used to prepare the compounds of this invention is illustrated by the following Scheme 1:

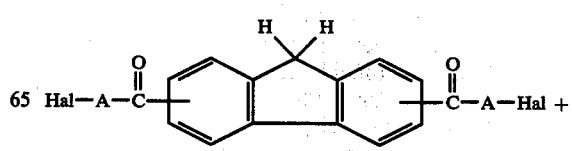

1

-continued

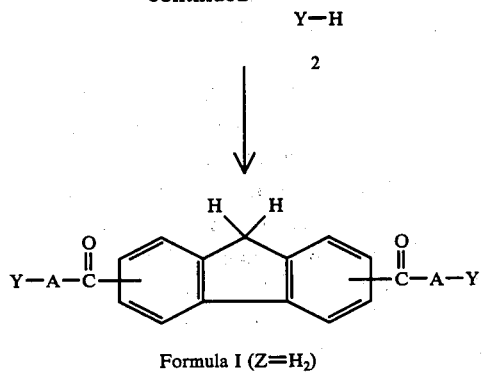

Formula I (Z=H$_2$)

In this reaction scheme A and Y have the meaning defined hereinbefore, and each Hal is either Cl, Br. or I.

The bis-(ω-haloacyl)fluorene derivatives, 1, in which the position of substitution is 2,7-, can be prepared by a Friedel-Crafts acylation of fluorene. Of suitable acylating agents which may be used there can be mentioned for example: chloroacetyl chloride, bromoacetyl bromide, 3-chloropropionyl chloride, 4-chlorobutyryl chloride, 5-chlorovalery chloride, 5-chloro-4-methylvalery chloride, 5-chloro-3-methylvaleryl chloride and the like.

It is obvious to those skilled in the art that the acylation reaction may be carried out in a variety of solvents and under catalysis of a variety of Lewis acids. The temperature and duration of the reaction may be varied to allow for optimum reaction conditions. A preferred procedure is to combine one equivalent of fluorene with 2.5 equivalents of an acrylating agent in methylene chloride followed by portionwise addition of aluminum chloride. The temperature of the reaction is maintained below zero degrees with continuous stirring. After the additions are complete the temperature may be elevated to 25° – 40° C for 12 to 36 hours. The reaction mixture is worked up in the usual manner by decomposing the complex with ice water/HCl. The product obtained is recrystallized from methylene chloride, chloroform, or the like. The procedure may be varied such that there is a reverse addition of acylating agent and Lewis acid, or a reverse addition of aromatic hydrocarbon and Lewis acid. The more reactive halogen derivative, that is, the bis(ω-iodoacyl)fluorene may be prepared from the corresponding bis-chloro derivative using a halogen exchange reaction under the conditions generally employed in the Conant-Finkelstein reaction.

Of typical amines, 2, useful in Scheme 1 there can be mentioned for example: ammonia, or a compound which is a potential source of ammonia such as, for example, hexamethylenetetramine and the like; primary amines such as ethylamine, propylamine and the like; and secondary amines such as diethylamine, dibutylamine, piperidine, 4-methylpiperidine, morpholine, piperazine, N-ethylpiperazine, 6-azabicyclo[3.2.1]octane and the like.

The amination of bis(ω-haloacyl)fluorene, 1, may be carried out under a variety of conditions. For example, compound 1 may be heated together with a large excess of the amine, 2, the excess amine serving as the reaction medium and the hydrohalide acceptor. This method is particularly suitable for readily available amines, the excess of which can be easily removed from the reaction mixture by, for example, distillation at reduced pressure or by washing the product with water. Or, one equivalent of compound 1 and four equivalents of the amine, 2, may be heated together in one of a number of different types of solvents, for example, in aromatic solvents such as benzene, toluene, xylene, and the like; or ethers such as tetrahydrofuran, dioxane and the like; or ketones such as acetone, butanone and the like; or aprotic solvents such as N,N-dimethylformamide, N,N-dimethylacetamide, dimethylsulfoxide and the like; or mixtures of these solvents with water. The reaction between compound 1 wherein the halogen is Cl and the amine, 2, is frequently promoted by the addition of either sodium or potassium iodide, the iodide being used in either catalytic or stoichiometric amounts. In some cases, it may be advantageous to use only two equivalents of the amine, 2, for each equivalent of the bis(ω-haloacyl)-fluorene, 1, an excess of an inorganic base such as powdered sodium or potassium carbonate being used as the hydrohalide acceptor. The reaction will proceed normally in 12 to 72 hours at temperatures of 20° to 150° C. As volatile amines are employed, the reaction is best carried out under pressure in a suitable pressure reactor or autoclave.

Alternately, the amination reaction may be carrier out on a derivative of compound 1 such as the bis-ketal fluorene derivative, which may be prepared by allowing bis(ω-halocyl)fluorene and an excess of ethyl orthoformate to react in the presence of an acid catalyst such as hydrochloric acid for several days in a polar solvent such as ethanol, tetrahydrofuran and the like.

The compounds of Formula I wherein A is an alkylene chain of 3 to 6 carbon atoms and Z is H$_2$ may also be prepared by the reaction of a Grignard reagent with a dinitrile of fluorene as represented by the following Scheme 2:

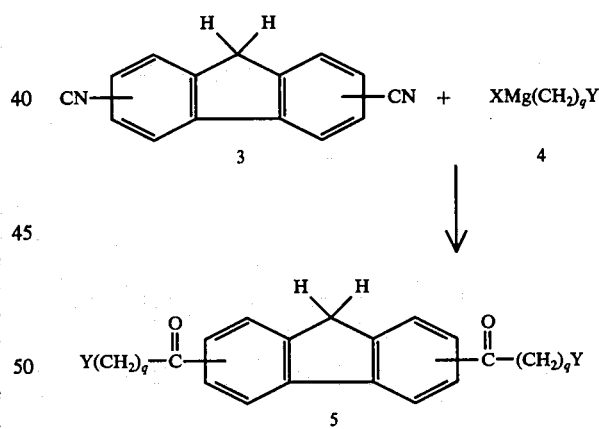

In the above reaction X is bromine or chlorine, $q$ is 3 to 6 and Y may be any of the groups defined hereinbefore except those which contain a hydrogen attached to the nitrogen atom.

The reaction will proceed in from 1 to 24 hours at a temperature ranging from room temperature to about 80° C. The Grignard reagent, 4, may be prepared by reacting magnesium and an aminoalkyl halide of the formula X(CH$_2$)$_q$Y wherein X, $q$, and Y have the meaning defined hereinabove. The preferred solvent for this reaction is usually tetrahydrofuran.

The dicyanofluorene derivative, 3, may be prepared from known fluorenediamines by a Sandmeyer reaction on the tetrazonium salts or from known fluorenedicarboxylic acids by dehydration of the corresponding amides by standard procedures.

The compounds of Formula I wherein Z is H₂ and A is —CH₂CH₂— may also be prepared by the Mannich reaction represented by the following Scheme 3:

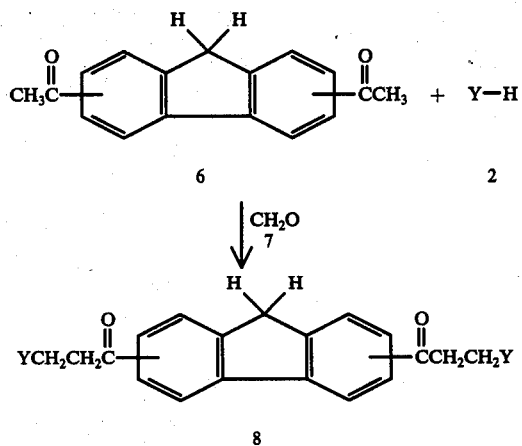

By combining one equivalent of compound 6 and two or more equivalents of compound 2 with three or more equivalents of formaldehyde, 7, the reaction will proceed in from 1 to 24 hours in solvents such as water, acetic acid, ethanol, butanol, dioxane, tetrahydrofuran and the like and at temperatures equivalent to the reflux temperature of the solvent. In this reaction either of two sources of formaldehyde may be employed. When formalin is used the reaction may be conducted with a suspension of compound 6 or a co-solvent such as methanol may be added to allow the reaction to proceed in a homogeneous medium. When the source of formaldehyde is paraformaldehyde the reaction is carried out in an organic solvent such as those mentioned above. It is sometimes desirable to add a slight excess of hydrochloric acid to promote depolymerization of paraformaldehyde either during the reaction or at the end of the reaction.

The secondary amine, compound 2, employed in this reaction may be added to the reaction medium as the hydrochloride salt or as the base form with subsequent in situ formation of the hydrochloride salt by the addition of hydrochloric acid. Of typical secondary amines which may be utilized in the above reaction there can be mentioned for example: dimethylamine, dibutylamine, piperidine, 4-methylpiperidine, morpholine, N-ethylpiperazine, 6-azabicyclo[3.2.1]octane and the like.

The diacetyl fluorene compound, 6, may be prepared by a Friedel-Crafts acylation reaction on fluorene or by a Grignard reaction of dicyanofluorene, 3, with methylmagnesium halide. The dicyanofluorene compound may be obtained by the methods described hereinbefore.

The compounds of Formula I wherein Z is oxygen may be prepared by oxidation of the corresponding fluorene bis-basic ketone compounds, as illustrated in the following Scheme 4:

This oxidation reaction may be carried out following the procedure of Y. Sprinzak [J.Am. Chem. Soc. 80, 5449(1958)] whereby oxygen is bubbled through a solution of fluorene in pyridine containing catalytic quantities of benzyltrimethylammonium hydroxide. The reaction is conducted at room temperature for a period of from 1 to 24 hours. Other strong bases, such as alcoholic KOH, NaOCH₃ and the like, which are capable of forming the carbanion at C-9 of fluorene may be used in place of benzyltrimethylammonium hydroxide. Also, other solvents such as acetone may be employed.

Alternatively, this reaction will proceed in from 15 minutes to 6 hours at a temperature of from 80° to 120° C using a dichromate anion, such as sodium dichromate or potassium dichromate, as the oxidizing agent. The amount of oxidizing agent is limited to the stoichiometric quantity required for oxidation of the 9-methylene group of the fluorene derivative. Suitable solvents for this conversion are for example water, acetic acid, tert-butyl alcohol and the like or combinations of these solvents. For example, by combining three equivalents of the fluorene derivative (Formula I where Z=H₂) dissolved in acetic acid with four equivalents of sodium dichromate and refluxing the mixture for 1 to 3 hours the corresponding fluorenone derivative (Formula I where Z=O) can be obtained. This oxidation reaction may also be carried out on the bis-(ω-haloacyl)fluorene derivative, compound 1, to give the corresponding fluorenone derivative, 8, as represented by the following reaction Scheme 5:

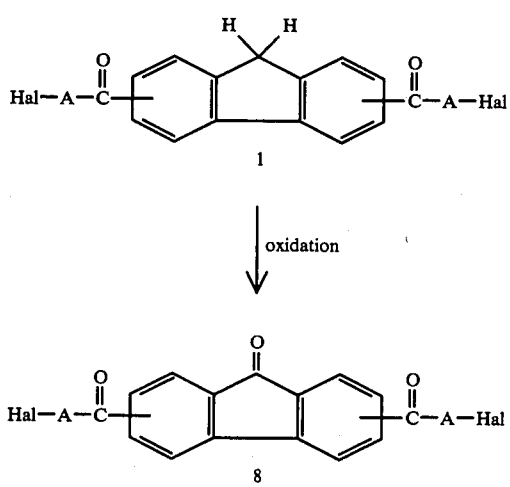

In the above reaction scheme Hal is either Cl or Br, and A has the meaning defined hereinbefore. Compound 8 may then be substituted for compound 1 in the amination reaction as outlined by Scheme 1.

Representative compounds of the present invention and several of the methods of preparing them, mentioned above, are illustrated in the following specific examples.

EXAMPLE 1

2,7-Bis(4-chlorobutyryl)fluorene

To a solution of 23.6g (0.142 mole) of fluorene and 50.0g (0.35 mole) of 4-chlorobutyryl chloride in 1500 ml of methylene chloride chilled to −20° C was added 39.8g (0.298 mole) of aluminum chloride with rapid stirring. The reaction mixture was refluxed four hours, stirred at room temperature for 16 hours, then poured onto ice/conc. Hcl. The organic layer was separated, washed with saturated sodium bicarbonate solution and dried over magnesium sulfate. After filtration, the methylene chloride solution was evaporated to dryness and the solid residue recrystallized from acetone to yield the desired product. M.P. 172°–175° C. $\lambda_{max}^{CHCl_3}$ 329, $E_{1cm}^{1\%}$ 971.

EXAMPLE 2

2,7-Bis(5-chlorovaleryl)fluorene

When 54.8g (0.354 mole) of 5-chlorovaleryl chloride is substituted for 4-chlorobutyryl chloride and the procedure of Example 1 is followed, 2,7-bis(5-chlorovaleryl)fluorene is obtained. M. P. 124°–125° C, $\lambda_{max}^{EtOH}$ 325, $E_{1cm}^{1\%}$ 936.

EXAMPLE 3

2,5-Dicyanofluorene

To one equivalent of 2,5-diaminofluorene [G. Morgan and R. Thomason, J. Chem. Soc., 2695 (1926)] dissolved in dilute hydrochloric acid and cooled to 0° C is added 2.2 equivalents of sodium nitrate, and the mixture is cautiously neutralized with sodium carbonate. This mixture is added portionwise to a cold solution of 2.5 equivalents of cuprous cyanide with stirring to give 2,5-dicyanofluorene which can be purified from a dimethylformamide-water combination. In like manner 2,7- and 3,6-dicyanofluorene may be prepared.

EXAMPLE 4

1,7-Dicyanofluorene

To a mixture of one equivalent of fluorene-1,7-dicarboxylic acid [Bamberger and Hooker, Ann. 229, 151,154,161 (1885)] and 2.2 equivalents of p-toluenesulfonamide is added 4.5 equivalents of phosphorus pentachloride. After the initial reaction has subsided the reaction mixture is heated to 200° C to remove the volatile secondary products. The solid residue remaining is cooled and treated with pyridine and water. The suspension is filtered, washed with water and suspended in dilute sodium hydroxide solution followed by filtration and washing with water to give 1,7-dicyanofluorene, which can be recrystallized from a dimethylformamide-water combination. In like manner 2,7-dicyanofluorene may be prepared.

EXAMPLE 5

By the method of Example 1, by substituting for 4-chlorobutyryl chloride, the appropriate molar equivalent amounts of 4-chlorovaleryl chloride, 4-chloro-2-methylbutyryl chloride or 5-chloro-3-methylvaleryl chloride, each of which can be prepared by treating respectively γ-valerolactone, α-methyl-γ-butyrolactone and β-methyl-δ-valerolactone with thionyl chloride and anhydrous zinc chloride [O.Wheeler and E. de Rodriguez, J. Org. Chem. 29, 1227 (1962)] the following compounds are prepared:

2,7-Bis(4-chlorovaleryl)fluorene
2,7-Bis(4-chloro-2-methylbutyryl)fluorene   2,7-Bis(5-chloro-3-methylvaleryl)fluorene.

EXAMPLE 6

2,7-Bis(3-piperidinopropionyl)fluorene Dihydrochloride

A mixture of 25.0g (0.1 mole) of 2,7-diacetylfluorene, 9.0g (0.3 mole) of paraformaldehyde, and 25.5g (0.21 mole) of piperidine hydrochloride in
200 ml of n-butyl alcohol was refluxed two hours. The solid which crystallized on cooling to room temperature was filtered and recrystallized twice from methanol-ethyl acetate and once from methanol-acetonitrile to yield the desired product. M.P. 236°–237° C, $\lambda_{max}^{EtOH}$ 328, $E_{1cm}^{1\%}$ 750.

EXAMPLE 7

2,7-Bis(4-piperidinobutyryl)fluorene

A mixture of 18.8g (0.05 mole) of 2,7-bis(4-chlorobutyryl)fluorene, prepared in Example 1, 34.0g (0.4 mole) of piperidine, 16.6g (0.1 mole) of potassium iodide in 200 ml of butanone was stirred and refluxed for three days. The reaction mixture was poured into 1000 ml of water, and the solid which precipitated was filtered and recrystallized twice from chloroformacetone to give the desired product. M.P. 157°–159° C, $\lambda_{max}^{0.1NHCl}$ 325, $E_{1cm}^{1\%}$ 816.

EXAMPLE 8

2,7-Bis(4-piperidinobutyryl)fluorene Dihydrochloride

By the procedure of Example 7, 2,7-bis(4-piperidinobutyryl)fluorene was prepared and dissolved in a chloroform-butanone mixture. The resulting solution was acidified with ethereal HCl, and the solid precipitate recrystallized three times from methanol-butanone to give the dihydrochloride salt. M.P. 286°–288° C, $\lambda_{maxhu\ H_2O}$ 325, $E_{1cm}^{1\%}$ 828.

EXAMPLE 9

2,7-Bis(4-morpholinobutyryl)fluorene

Following the procedure of Example 7 only substituting for piperidine, 34.9g (0.4 mole) of morpholine, the desired product was obtained which was recrystallized twice from chloroform-acetone. M.P. 166.5°–168.5° C, $\lambda_{max}^{0.1NHCl}$ 325, $E_{1cm}^{1\%}$ 828.

EXAMPLE 10

2,7-Bis(5-Morpholinovaleryl)fluorene

By the procedure of Example 7, 20.2g (0.05 mole) of 2,7-bis(5-chlorovaleryl)fluorene, prepared in Example 2, 34.9g (0.4 mole) of morpholine were reacted to give the desired product which was recrystallized twice from methylene chloride-methanol. M.P. 134°–136.5° C, $\lambda_{max}^{0.1NHCl}$ 325, $E_{1cm}^{1\%}$ 776.

EXAMPLE 11

2,7-Bis(5-piperidinovaleryl)fluorene

By the procedure of Example 7, 20.2g (0.05 mole) of 2,7-bis(5-chlorovaleryl)fluorene, prepared in Example 2, and 34.0g (0.4mole) of piperidine were reacted. The solid precipitate was recrystallized twice from methanol and chromatographed on alumina. Evaporation of solvent from the fraction collected gave the desired product. M.P. 124°–127° C, $\lambda_{max}^{CHCl_3}$ 328, $E_{1cm}^{1\%}$ 731.

EXAMPLE 12

2,7-Bis(5-piperidinovaleryl)fluorene Dihydrochloride

By the procedure of Example 11, 2,7-bis(5-piperidinovaleryl)fluorene was prepared and dissolved in ether then treated with ethereal HCl to give the desired product which was recrystallized twice from methanolethyl acetate. M.P. 268°–270° C, $\lambda_{max}^{EtOH}$ 324, $E_{1cm}^{1\%}$ 577.8.

EXAMPLE 13

2,7-Bis[4-(4-methylpiperidino)butyryl]fluorene

Following the procedure of Example 7 only substituting for piperidine, 39.6g (0.4 mole) of 4-methylpiperidine, the desired product was obtained which was recrystallized twice from chloroform-acetone. M.P. 179.5°–181° C, $\lambda_{max}^{CHCl_3}$ 328, $E_{1cm}^{1\%}$ 731.

EXAMPLE 14

2,7-bis[4-(4-benzylpiperidino)butyryl]fluorene

Following the procedure of Example 7 only substituting for piperidine, 70.0g (0.4 mole) of 4-benzylpiperidine, the desired product was obtained which was recrystallized from chloroform-acetone. M.P. 135°–137° C, $\lambda_{max}^{CHCl_3}$ 329, $E_{1cm}^{1\%}$ 571.

EXAMPLE 15

2,7-bis[4-(4-phenylpiperidino)butyryl]fluorene

Following the procedure of Example 7 only substituting for piperidine, 65.0g (0.4 mole) of 4-phenylpiperidine, the desired product was obtained which was recrystallized twice from chloroform-acetone. M.P. 190°–192° C, $\lambda_{max}^{CHCl_3}$ 330, $E_{1cm}^{1\%}$ 595.

EXAMPLE 16

2,7-bis[5-(diethylamino)valeryl]fluorene

A mixture of 30.0g (0.074 mole) of 2,7-bis(5-chlorovaleryl)fluorene, prepared in Example 2, 2.0g of potassium iodide, 200 ml of diethylamine and 100 ml of THF was stirred and heated in a Paar bomb at 120° C for 24 hours. The reaction mixture was combined with 300 ml of water, and the volume concentrated to 100 ml. Following the addition of 300 ml of water, the resulting precipitate was filtered and recrystallized once from etheracetone and once from ether to yield the desired product. M.P. 78°–80° C, $\lambda_{max}^{EtOH}$ 326, $E_{1cm}^{1\%}$ 801.

EXAMPLE 17

2,7-bis[5-(diethylamino)valeryl]fluorene bis-dihydrogen citrate

By the procedure of Example 16, 2,7-bis[5-(diethylamino)valeryl]fluorene was prepared and treated with 2 equivalents of citric acid in hot butanone to give the desired product which was recrystallized from methanolbutanone.

EXAMPLE 18

2,7-bis[5-(4-methylpiperidino)valeryl]fluorene

Following the procedure of Example 7, 20.2g (0.05 mole) of 2,7-bis(5-chlorovaleryl)fluorene, prepared in Example 2, and 39.6g (0.4 mole) of 4-methylpiperidine were reacted to give the desired product which was recrystallized three times from chloroform-acetone. M.P. 143°–144.5° C, $\lambda_{max}^{CHCl_3}$ 329, $E_{1cm}^{1\%}$ 731.

EXAMPLE 19

2,7-bis[5-(4-benzylpiperidino)valeryl]fluorene

Following the procedure of Example 7, 20.2g (0.05 mole) of 2,7-bis(5-chlorovaleryl)fluorene, prepared in Example 2, and 70.0g (0.4 mole) of 4-benzylpiperidine were reacted to give the desired product which was recrystallized three times from chloroform-acetone. M.P. 147°–149° C, $\lambda_{max}^{EtOH}$ 329, $E_{1cm}^{1\%}$ 577.

EXAMPLE 20

2,7-bis[5-(dimethylamino)valeryl]fluorene

A mixture of 38.0g (0.095 mole) of 2,7-bis(5-chlorovaleryl)fluorene, prepared in Example 2, 2.0g potassium iodide, 250 ml 40% aqueous dimethyl amine, and 100 ml THF was stirred and heated in a Paar bomb at 102° C for seventeen hours. The volume of the reaction mixture was concentrated to 100 ml, and 500 ml of water were added. The solid which precipitated was filtered, recrystallized once from methylene chloride-petroleum ether, chromatographed on alumina using chloroform as the eluant, then recrystallized once from chloroform-petroleum ether to give the desired product. M.P. 124°–126° C, $\lambda_{max}^{EtOH}$ 325, $E_{1cm}^{1\%}$ 897.

EXAMPLE 21

2,7-bis[4-(diethylamino)butyryl]fluorene

Following the procedure of Example 16 only substituting for 2,7-bis(5-chlorovaleryl)fluorene, 27.8g (0.074 mole) of 2,7-bis(4-chlorobutyryl)fluorene, prepared in Example 1, the solid obtained was chromatographed on alumina using ether as the eluant, then recrystallized twice from etherpentane to give the desired product. M.P. 79°–81° C, $\lambda_{max}^{EtOH}$ 327, $E_{1cm}^{1\%}$ 846.

EXAMPLE 22

2,7-bis[5-(dibutylamino)valeryl]fluorene

Following the procedure of Example 16 only substituting for diethylamine 150 ml of dibutylamine the solid obtained was purified by chromatography on alumina using methylene chloride as the eluant to yield the desired product. M.P. 48°–50° C, $\lambda_{max}^{EtOH}$ 320, $E_{1cm}^{1\%}$ 612.

EXAMPLE 23

2,7-bis(diethylaminoacetyl)fluorene dihydrochloride

A mixture of 250 ml of tetrahydrofuran, 14.0g (0.044 mole) of 2,7-bis(chloroacetyl)fluorene and 100 ml of diethylamine, previously cooled to 0° C, was stirred at room temperature for 54 hours, filtered and the filtrate evaporated to dryness. The residue was dissolved in ethanol, and this solution was treated with excess ethanolic hydrogen chloride to yield the dihydrochloride salt. The product was precipitated by the addition of a large volume of ether and purified by recrystallization from methanolethyl acetate. M.P. 225°–228° C, $\lambda_{max}^{EtOH}$ 337, $E_{1cm}^{1\%}$ 914.

EXAMPLE 24

2,7-bis(piperidinoacetyl)fluorene dihydrochloride

A mixture of 19.0g (0.06 mole) of 2,7-bis(chloroacetyl)fluorene, 10.2g (0.12 mole) of piperidine and 25.4g (0.24 mole) of sodium carbonate in 300 ml of tetrahydrofuran was gently refluxed with stirring for 36 hours then filtered and concentrated in vacuo. The residue was extracted with ether and this solution was treated with ethereal hydrogen chloride to give the desired product which was recrystallized from methanol-butanone-ether. M.P. 302°–304° C (dec.), $\lambda_{max}^{H_2O}$ 337, $E_{1cm}^{1\%}$ 834.

EXAMPLE 25

2,7-bis(dimethylaminoacetyl)flourene dihydrochloride

A mixture of 18.5g (0.058 mole) of 2,7-bis(chloroacetyl)fluorene and 38.0g (0.84 mole) of dimethylamine in 350 ml of tetrahydrofuran was heated with stirring at 60° C for 24 hours in a Paar general purpose bomb. After cooling, the reaction mixture was filtered, concentrated in vacuo and the residue extracted with ether. The ether solution was treated with ethereal hydrogen chloride to yield the desired product which was purified by recrystallization from ethanol-butanone. M.P. 296°–298° C (dec).

EXAMPLE 26

3,6-bis(4-piperidinobutyryl)fluorene dihydrochloride

To a solution of 2.5 equivalents of 3-piperidinopropyl magnesium chloride, prepared from magnesium and 3-piperidinopropylchloride in tetrahydrofuran, is added dropwise a solution of 1 equivalent of 2,6-dicyanofluorene, prepared as in Example 4, dissolved in tetrahydrofuran. After the addition is complete the mixture is gently refluxed for 2 hours and stirred at room temperature for an additional 4 hours. The Grignard complex is decomposed by treating the reaction mixture dropwise with a saturated solution of ammonium chloride until the precipitation of magnesium salt is complete. The mixture is filtered and the filtrate is concentrated in vacuo. The residue is dissolved in dilute hydrochloric acid with warming then filtered. The aqueous solution is made alkaline and extracted with several portions of ether. The ether layers are combined, dried over magnesium sulfate and treated with ethereal hydrogen chloride to give the desired product which can be recrystallized from methanol-ethyl acetate.

EXAMPLE 27

By the method of Example 26, but substituting for 3,6-dicyanofluorene, the appropriate molar equivalent amounts of 2,5-dicyanofluorene or 2,7-dicyanofluorene the following compounds are prepared:

2,5-Bis(4-piperidinobutyryl)fluorene dihydrochloride
2,7-Bis(4-piperidinobutyryl)fluorene dihydrochloride.

EXAMPLE 28

2,7-bis[4-(3-azabicyclo[3.2.2]nonan-3-yl)butyryl]fluorene

A mixture of 11.25g (0.03 mole) of 2,7-bis(4-chlorobutyryl)fluorene, 30.1g (0.24 mole) of 3-azabicyclo[3.2.2]nonane and 10.0g (0.06 mole) of potassium iodide in 200 ml butanone is heated at reflux with stirring for 3 days. The reaction mixture was poured into 1000 ml of water, and the resulting solid precipitate filtered and recrystallized from chloroform-acetone to yield the desired product.

EXAMPLE 29

2,7-Bis(4-Aminobutyryl)Fluorene Dihydrochloride

An ethanolic solution of 1 equivalent of 2,7-bis(4-chlorobutyryl)fluorene and 2.4 equivalents of hexamethylenetetramine were reacted at reflux for 36 hours. The solution was acidified with 3N HCl, digested for several hours and the solvent removed under reduced pressure to give the desired product which can be recrystallized from methanol-ethyl acetate.

EXAMPLE 30

2,7-Bis(4-Ethylaminobutyryl)Fluorene Dihydrochloride

By the procedure of Example 29 only substituting for hexamethylenetetramine, a hundred fold excess of ethylamine, the desired product can be obtained.

EXAMPLE 31

By the method of Example 7, but substituting for piperidine, the appropriate molar equivalent amounts of N-methylpiperazine, diallylamine, N-methylcyclohexylamine, 4-propylpiperidine or pyrrolidine the following compounds are prepared:

2,7-Bis[4-(N-methylpiperazino)butyryl]fluorene
2,7-Bis(4-diallylaminobutyryl)fluorene
2,7-Bis[4-(N-methylcyclohexylamino)butyryl]fluorene
2,7-Bis[4-(4-propylpiperidino)butyryl]fluorene
2,7-Bis(4-pyrrolidinobutyryl)fluorene.

EXAMPLE 32

By the method of Example 11, but substituting for 2,7-bis(5-chlorovaleryl)fluorene, the appropriate molar equivalent amounts of 2,7-bis(4-chlorovaleryl)fluorene, 2,7-bis(4-chloroisovaleryl)fluorene or 2,7-bis(5-chloro-3-methylvaleryl)fluorene the following compounds are prepared:

2,7-Bis(4-piperidinovaleryl)fluorene
2,7-Bis(4-piperidinoisovaleryl)fluorene
2,7-Bis(5-piperidino-3-methylvaleryl)fluorene.

EXAMPLE 33

2,7-Bis(4-Piperidinobutyryl)Fluoren-9-One

A solution of 9.0g (0.019 mole) 2,7-bis(4-piperidinobutyryl)fluorene, prepared in Example 7, 7.54g (0.0253 mole) sodium dichromate and 300 ml of glacial acetic acid was stirred and refluxed for one hour. The reaction mixture was evaporated to semi-dryness and made basic using concentrated ammonium hydroxide. The solid which precipitated was filtered, washed with water, and chromatographed on alumina using chloroform as the eluant. The solvent was removed from the fraction collected, leaving a solid residue which was recrystallized three times from chloroform-acetone to yield the desired product. M.P. 168°–170° C, $\lambda_{max}^{CHCl_3}$ 281, $E_{1cm}^{1\%}$ 1579.

EXAMPLE 34

2,7-Bis(4-Piperidinobutyryl)Fluoren-9-One Dihydrochloride 2,7-Bis(4-piperidinobutyryl)fluoren-9-one, prepared in Example 33, was dissolved in chloroform and the resulting solution acidified with ethereal HCl to give the desired product which was recrystallized once from water-isopropyl alcohol. M.P. 322°–323° C, $\lambda_{Max}^{H_2O}$ 284, $E_{1cm}^{1\%}$ 1,220.

EXAMPLE 35

2,7-Bis[5-(Diethylamino)Valeryl]Fluoren-9-one

A solution of 12.0g (0.025 mole) 2,7-bis[5-(diethylamino)valeryl]-fluorene, prepared in Example 16, 2.0 ml 40% benzyltrimethylammonium hydroxide in pyridine and 200 ml pyridine was stirred at room temperature while oxygen was bubbled through the solution at a rate of 500 ml/min. for a total of four hours. The reaction mixture was evaporated to dryness leaving a residue which was chromatographed on alumina using chloroform as the eluant. The solvent was removed from the fraction collected leaving a solid which was recrystallized once from chloroform-petroleum ether to yield the desired product. M.P. 108°–109.5° C, $\lambda_{max}^{EtOH}$ 280, $E_{1cm}^{1\%}$ 1530.

EXAMPLE 36

2,7-Bis[4-(4-Methylpiperidino)Butyryl]Fluoren-9-One

Following the procedure of Example 35 and substituting 12.5g (0.025 mole) of 2,7-bis[4-(4-methylpiperidino)butyryl]fluorene, prepared in Example 13, the solid obtained was recrystallized three times from chloroform-acetone to give the desired product. M.P. 178°–180° C, $\lambda_{max}^{EtOH}$ 279, $E_{1cm}^{1\%}$ 1480.

EXAMPLE 37

2,7-Bis[4-(4-Methylpiperidino)butyryl]Fluoren-9-One Bis-Dihydrogen Citrate

By treating 2,7-bis[4-(4-methylpiperidino)butyryl]-fluoren-9-one, prepared in Example 36, with 2 equivalents of citric acid in hot butanone, the desired product was obtained which was recrystallized from methanol-butanone.

EXAMPLE 38

2,7-Bis(5-Morpholinovaleryl)Fluoren-9-One

Following the procedure of Example 35 and substituting 12.6g (0.025 mole) of 2,7-bis(5-morpholinovaleryl)fluorene, prepared in Example 10, the solid obtained was recrystallized twice from chloroform-acetone to yield the desired product. M.P. 145.5°–147.5° C, $\lambda_{max}^{EtOH}$ 280, $E_{1cm}^{1\%}$ 1450.

EXAMPLE 39

2,7-Bis[5-(4-Benzylpiperidino)Valeryl]Fluoren-9-One

Following the procedure of Example 35 and substituting 17.0g (0.025 mole) of 2,7-bis[5-(4-benzylipiperidino)valeryl]fluorene, prepared in Example 19, the solid obtained was recrystallized twice from chloroformacetone to yield the desired product. M.P. 124°–126° C, $\lambda_{max}^{EtOH}$ 279, $E_{1cm}^{1\%}$ 1170.

EXAMPLE 40

2,7-Bis[4-(4-Benzylpiperidino)Butyryl]Fluoren-9-One

Following the procedure of Example 35 and substituting 16.3g (0.025 mole) of 2,7-bis[4-(4-benzylpiperidino)butyryl]fluorene, prepared in Example 14, the solid obtained was recrystallized twice from chloroform-acetone to yield the desired product. M.P. 141°–143° C, $\lambda_{max}^{CHCl_3}$ 281, $E_{1cm}^{1\%}$ 1200.

EXAMPLE 41

2,7-Bis 8 5-(4-methylpiperidino)valeryl]fluoren-9-one

Following the procedure of Example 35 and substituting 13.2g (0.025 mole) of 2,7-bis[5-(4-methylpiperidino)valeryl]fluorene, prepared in Example 18, the solid obtained was recrystallized twice from chloroformacetone to yield the desired product. M.P. 150.5°–152.5° C, $\lambda_{max}^{CHCl_3}$ 282, $E_{1cm}^{1\%}$ 1490.

EXAMPLE 42

2,7-bis[5-(dimethylamino)valeryl]fluoren-9-one

Following the procedure of Example 35 and substituting 10.5g (0.025 mole) of 2,7-bis[5-(dimethylamino)-valeryl]fluorene, prepared in Example 20, the solid obtained on workup was recrystallized once from chloroform-petroleum ether to yield the desired product. M.P. 149.5°–151° C, $\lambda_{max}^{EtOH}$ 280, $E_{1cm}^{1\%}$ 932.

EXAMPLE 43

2,7-bis(4-morpholinobutyryl)fluoren-9-one

Following the procedure of Example 35 and substituting 11.9g (0.025 mole) of 2,7-bis(4-morpholinobutyryl)fluorene, prepared in Example 9, the solid obtained was recrystallized four times from chloroform-acetone to yield the desired product. M.P. 174°–175.5° C, $\lambda_{max}^{CHCl_3}$ 280, $E_{1cm}^{1\%}$ 1610.

EXAMPLE 44

2,7-bis[4-(diethylamino)butyryl]fluoren-9-one dihydrochloride

Following the procedure of Example 35 and substituting 11.2g (0.025 mole) of 2,7-bis[4-(diethylamino)-butyryl]fluorene, prepared in Example 21, 2,7-bis[4-(diethylamino)butyryl]fluoren-9-one was obtained. This free base was dissolved in chloroform and treated with ethereal HCl to give the corresponding dihydrochloride salt which was recrystallized twice from methanol-ethyl acetate. M.P. 275° C. $\lambda_{max}^{EtOH}$ 281, $E_{1cm}^{1\%}$ 1230.

EXAMPLE 45

2,7-Bis(chloroacetyl)fluoren-9-one

A mixture of 5.0g (0.016 mole) of 2,7-bis(chloroacetyl)fluorene, 6.3g (0.020 mole) of sodium dichromate and 125 ml of glacial acetic acid was refluxed with stirring for seventeen hours. The resulting precipitate was filtered while the solution was hot, then washed with acetic acid and dried in vacuo to yield the desired product.

EXAMPLE 46

2,7-Bis(dimethylaminoacetyl)fluoren-9-one

A mixture of 15.0g (0.045 mole) of 2,7-bis(chloroacety)fluoren-9-one, 100 ml of 40% dimethylamine and 7.0g of potassium iodide in 200 ml of butanone was placed in a Paar bomb and heated at 70°-80° C with stirring for 2 hours. The reaction mixture was cooled and poured into 2.0 l of ice water, and the solid which precipitated was filtered off, dissolved in chloroform and dried over magnesium sulfate to give the desired product.

In like manner, but substituting for dimethylamine, the appropriate molar equivalent amounts of diethylamine and piperidine the following compounds are prepared:

2,7-Bis(diethylaminoacetyl)fluoren-9-one
2,7-Bis(piperidinoacetyl)fluoren-9-one.

What is claimed is:

1. A compound selected from a base of the formula

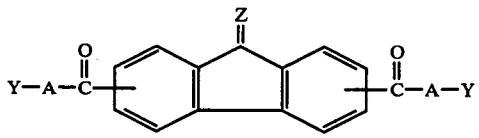

wherein Z is a member selected from the group consisting of oxygen or H$_2$; each A is a straight or branched alkylene chain of from 1 to 6 carbon atoms; and each Y is a member selected from the group consisting of A. the group

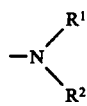

wherein R$^1$ and R$^2$ are individually selected from the group consisting of hydrogen, (lower)alkyl having from 1 to 6 carbon atoms, cycloalkyl having from 3 to 6 carbon atoms, alkenyl of from 3 to 6 carbon atoms and having the vinyl unsaturation in other than the 1-position of the alkenyl group;

B. the group

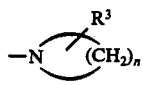

wherein n is a whole integer from 4 to 6, and R$^3$ is a member selected from the group consisting of hydrogen, (lower)alkyl of 1 to 4 carbon atoms, phenyl, or benzyl and can be linked to any one of the carbon atoms of the heterocyclic group; and C. the group

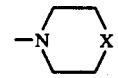

wherein X is a member selected from the group consisting of oxygen or NR$^4$, and R$^4$ is hydrogen or (lower)alkyl of from 1 to 4 carbon atoms;

or a pharmaceutically acceptable acid addition salt of said base.

2. A compound selected from a base of the formula

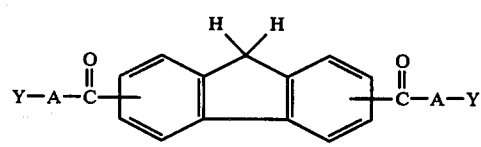

wherein: each A is a straight or branched alkylene chain of from 1 to 6 carbon atoms; and each Y is a member selected from the group consisting of A. the group

wherein R$^1$ and R$^2$ are individually selected from the group consisting of hydrogen, (lower)alkyl having from 1 to 6 carbon atoms, cycloalkyl having from 3 to 6 carbon atoms, alkenyl of from 3 to 6 carbon atoms and having the vinyl unsaturation in other than the 1-position of the alkenyl group;

B. the group

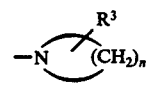

wherein n is a whole integer from 4 to 6, and R$^3$ is a member selected from the group consisting of hydrogen, (lower)alkyl of 1 to 4 carbon atoms, phenyl, or benzyl and can be linked to any one of the carbon atoms of the heterocyclic group; and C. the group

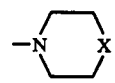

wherein X is a member selected from the group consisting of oxygen or NR$^4$, and R$^4$ is hydrogen or (lower)alkyl of from 1 to 4 carbon atoms;

or a pharmaceutically acceptable acid addition salt of said base.

3. A compound of claim 2 wherein each Y is the group

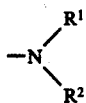

and one of said

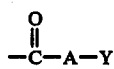

groups is in the 2-position of the tricyclic ring system and the remaining

group is in the 7-position of the tricyclic ring system.

4. A compound of claim 3 wherein each $R^1$ and $R^2$ is (lower)alkyl.

5. A compound of claim 2 wherein each Y is the group

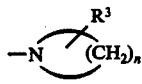

and one of said

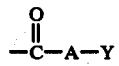

groups is in the 2-position of the tricyclic ring system and the remaining

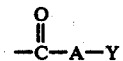

group is in the 7-position of the tricyclic ring system.

6. A compound of claim 5 wherein n is the integer 5.

7. A compound of claim 2 wherein each Y is the group

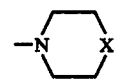

and one of said

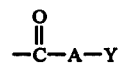

groups is in the 2-position of the tricyclic ring system and the remaining

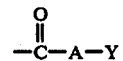

group is in the 7-position of the tricyclic ring system.

8. A compound of claim 2 which is 2,7-bis(4-piperidinobutyryl)fluorene or a pharmaceutically acceptable acid addition salt thereof.

9. A compound of claim 2 which is 2,7-bis[4-(4-methylpiperidino)butyryl]fluorene or a pharmaceutically acceptable acid addition salt thereof.

10. A compound of claim 2 which is 2,7-bis(4-diethylaminobutyryl)fluorene or a pharmaceutically acceptable acid addition salt thereof.

11. A compound of claim 2 which is 2,7-bis(diethylaminoacetyl)fluorene or a pharmaceutically acceptable acid addition salt thereof.

12. A compound of claim 2 which is 2,7-bis(piperidinoacetyl)fluorene or a pharmaceutically acceptable acid addition salt thereof.

13. A compound of claim 2 which is 2,7-bis(5-diethylaminovaleryl)fluorene or a pharmaceutically acceptable acid addition salt thereof.

14. A compound of claim 2 which is 2,7-bis(4-morpholinobutyryl)fluorene or a pharmaceutically acceptable acid addition salt thereof.

15. A compound of claim 2 which is 2,7-bis[4-(4-benzylpiperidino)butyryl]fluorene or a pharmaceutically acceptable acid addition salt thereof.

16. A compound selected from a base of the formula

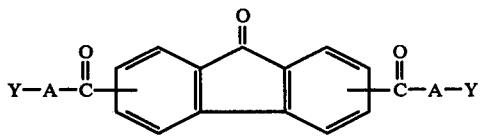

wherein: each A is a straight or branched alkylene chain of from 1 to 6 carbon atoms; and each Y is a member selected from the group consisting of A. the group

wherein $R^1$ and $R^2$ are individually hydrogen, (lower)alkyl having from 1 to 6 carbon atoms, cycloalkyl having from 3 to 6 carbon atoms, alkenyl of from 3 to 6 carbon atoms and having the vinyl unsaturation in other than the 1-position of the alkenyl group; or B. the group

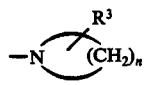

wherein n is a whole integer from 4 to 6, and $R^3$ is hydrogen, (lower)alkyl of 1 to 4 carbon atoms, phenyl, or benzyl and can be linked to any one of the carbon atoms of the heterocyclic group; or C. the group

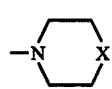

wherein X is oxygen or $NR^4$, and $R^4$ is hydrogen or (lower)alkyl of from 1 to 4 carbon atoms;

or a pharmaceutically acceptable acid addition salt of said base.

17. A compound of claim 16 wherein each Y is the group

and one of said

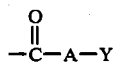

groups is in the 2-position of the tricyclic ring system and the remaining

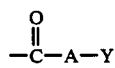

group is in the 7-position of the tricyclic ring system.

18. A compound of claim 17 wherein each R¹ and R² is (lower)alkyl.

19. A compound of claim 16 wherein each Y is the group

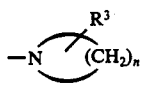

and one of said

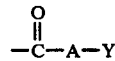

groups is in the 2-position of the tricyclic ring system and the remaining

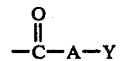

group is in the 7-position.

20. A compound of claim 19 wherein n is the integer 5.

21. A compound of claim 16 wherein each Y is the group

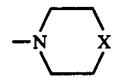

and one of said

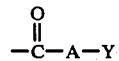

groups is in the 2-position of the tricyclic ring system and the remaining

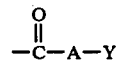

group is in the 7-position of the tricyclic ring system.

22. A compound of claim 16 which is 2,7-bis(4-piperidinobutyryl)fluorenone or a pharmaceutically acceptable acid addition salt thereof.

23. A compound of claim 16 which is 2,7-bis[5-(4-benzylpiperidino)valeryl]fluorenone or a pharmaceutically acceptable acid addition salt thereof.

24. A compound of claim 16 which is 2,7-bis(5-diethylaminovaleryl)fluorenone or a pharmaceutically acceptable acid addition salt thereof.

25. A compound of claim 16 which is 2,7-bis(4-morpholinobutyryl)fluorenone or a pharmaceutically acceptable acid addition salt thereof.

26. A compound of claim 16 which is 2,7-bis(5-dimethylaminovaleryl)fluorenone or a pharmaceutically acceptable acid addition salt thereof.

27. A compound of claim 16 which is 2,7-bis[4-(4methylpiperidino)butyryl]fluorenone or a pharmaceutically acceptable acid addition salt thereof.

* * * * *

UNITED STATES PATENT AND TRADEMARK OFFICE
CERTIFICATE OF CORRECTION

PATENT NO. : 4,064,347
DATED : December 20, 1977
INVENTOR(S) : R.W. Fleming, A.D. Sill and W.L. Albrecht It is certified that error appears in the above-identified patent and that said Letters Patent are hereby corrected as shown below:

Column 4, line 40, "alkyl" should read "allyl". Column 5, line 7, "hereto" should read "hetero". Column 7, line 25, "5-chlorovalerychloride" should read "5-chlorovalerylchloride; lines 25-26, "4-methylvalerychloride" should read "4-methylvalerylchloride"; line 34, "acrylating" should read "acylating". Column 8, line 24, "carrier" should read "carried"; line 27, "(ω-halocyl" should read "(ω-haloacyl)". Column 12, line 29, "(1962)" should read "(1964)". Column 18, line 31, "2,7-Bis85-(4-" should read "2,7-Bis[5-(4-".

Signed and Sealed this

Twenty-ninth Day of August 1978

[SEAL]

Attest:

RUTH C. MASON
Attesting Officer

DONALD W. BANNER
Commissioner of Patents and Trademarks